United States Patent [19]

Koegel et al.

[11] Patent Number: 4,620,538

[45] Date of Patent: Nov. 4, 1986

[54] LIGHT-WEIGHT OXYGEN DELIVERY HOOD ASSEMBLY FOR HYPERBARIC CHAMBER

[75] Inventors: Ewald Koegel, San Antonio, Tex.; Paul J. Sheffield, Beale AFB, Calif.

[73] Assignee: The United States of America as represented by the Secretary of the Air Force, Washington, D.C.

[21] Appl. No.: 713,666

[22] Filed: Mar. 19, 1985

[51] Int. Cl.⁴ ............................................. A61H 31/00
[52] U.S. Cl. .................................. 128/201.23; 128/30; 128/205.26
[58] Field of Search ............ 128/201.23–201.29, 128/202.19, 30, 30.2, 205.26

[56] References Cited

U.S. PATENT DOCUMENTS

| | | | |
|---|---|---|---|
| 594,945 | 12/1897 | Gordon | 128/201.27 |
| 1,215,327 | 2/1917 | Ackerman | 128/30 |
| 2,970,593 | 2/1961 | Seeler | 128/201.23 |
| 3,505,997 | 4/1970 | Cowley | 128/145.8 |
| 3,786,809 | 1/1974 | Kitrilakis | 128/191 |
| 4,186,735 | 2/1980 | Henneman et al. | 128/201.25 |
| 4,215,437 | 8/1980 | Kao | 128/201.25 |
| 4,297,999 | 11/1981 | Kitrell | 128/205.16 |
| 4,331,141 | 5/1982 | Pokhis | 128/204.28 |
| 4,407,280 | 10/1983 | Trammell et al. | 128/205.26 |
| 4,444,183 | 4/1984 | Heckendorn | 128/205.26 |

Primary Examiner—Henry J. Recla
Attorney, Agent, or Firm—Jules J. Morris; Donald J. Singer; James E. Maslow

[57] ABSTRACT

A light-weight hyperbaric oxygen therapy hood assembly comprising a neckdam and hood having a gas inlet and outlet. The neckdam comprises a diaphragm which can be varied from an open to a closed condition for sealing of the neckdam around the neck of the patient, the diaphragm being concentric to the hood and neckdam. An inflatable bladder is providable at the back of the hood. A check valve is affixable to the gas outlet of the hood.

5 Claims, 6 Drawing Figures

LIGHT-WEIGHT OXYGEN DELIVERY HOOD ASSEMBLY FOR HYPERBARIC CHAMBER

STATEMENT OF GOVERNMENT INTEREST

The invention described herein may be manufactured and used by or for the Government for governmental purposes without the payment of any royalty thereon.

BACKGROUND OF THE INVENTION

The present invention relates to hyperbaric oxygen therapy, and more particularly, to an improved and light-weight oxygen delivery hood assembly for patients in hyperbaric chambers.

Hyperbaric oxygen therapy is intermittent, short-term, high-dose oxygen therapy. In this treatment, patients are exposed to increased barometric pressure inside rigid walled chambers so that oxygen may be breathed at higher doses than otherwise attainable. This results in a large increase in the partial pressure of oxygen physically dissolved in the plasma. For example, breathing air at sea level results in an arterial oxygen tension of about 100 mm Hg, with virtually all of the oxygen being carried in combination with hemoglobin. Breathing 100 percent oxygen at 3 atmospheres absolute (ATA) equivalent to barometric pressure at 66 feet of sea water, results in an arterial oxygen tension of about 200 mm Hg. In addition to the oxygen transported by hemoglobin, up to six volumes percent oxygen is carried in a dissolved state. This increased tissue oxygen tension increases the oxygen diffusion gradient and enhances oxygen delivery to relatively ischemic tissue. This is an important factor in the adjunctive therapy of a number of medical disorders. With this treatment, oxygen is being employed as a drug, with the dosage (time and pressure) varying according to the medical disorder being treated.

Hyperbaric oxygen therapy has been successful in treatment of decompression sickness, arterial or venous gas embolism, clostridial myonecrosis (gas gangrene) and clostridial cellulitis, carbon monoxide poisioning, chronic osteomyelitis, osteomyelitis maxillofacial, and for promotion of granulation tissue formation, neovascularization and re-epithelialization in non-healing wounds.

Under current practice, some fully ambulatory patients can breathe 100% oxygen from a mask assembly while pressurized in a hyperbaric chamber at a desired pressure. However, many patients are equipped with medical facial appliances which prevent them from receiving oxygen by mask. Rather, the entire head must be enclosed in an oxygen environment, such as in a hood.

Furthermore, during the process of oxygen delivery, it is essential that an adequate seal be made between the chamber atmosphere and the breathing atmosphere to ensure that the patient receives 100% oxygen and to ensure against leakage of the oxygen into the chamber environment. It is also important to be able to open the oxygen delivery system or to be able to remove it rapidly and without difficulty in order to provide proper medical management of seriously ill patients.

Under current practice, a patient's head will be placed in a plastic hood assembly which is taped to the shoulders of the patient. This method of hood delivery invariably results in tape burns to the patient after daily use for any extented period. It also permits leakage of oxygen into the chamber environment.

It is therefore an object of the present invention to provide a hood which can be rapidly donned or doffed by the patient or by an assistant.

It is therefore an object of the present invention to provide a hood which avoids infliction of tape burns upon the patient over long durations of wear.

It is therefore an object of the present invention to provide a hood which limits leakage of oxygen into the hyperbaric chamber environment.

It is therefore an object of the present invention to provide a hood which has the ability to deliver 100% oxygen to patients with facial deformities and facial medical appliances.

It is another object of the present invention to provide a hood with inflatable means for support of the head of a patient who is treated in the reclining position.

SUMMARY OF THE INVENTION

The present invention provides a light-weight hyperbaric oxygen therapy hood assembly comprising a hood having a gas inlet and outlet. The neckdam diaphragm can be varied from an open to a closed condition for sealing of the neckdam around the neck of the patient, the diaphragm being concentric to the hood and neckdam. An inflatable bladder is providable at the back of the hood. A check valve is affixable to the gas outlet of the hood.

BRIEF DESCRIPTION OF THE DRAWINGS

The invention will be more clearly understood by reference to the following detailed description of a preferred embodiment thereof in conjunction with the accompanying drawings, in which.

DETAILED DESCRIPTION OF THE DRAWINGS

Figure 1:
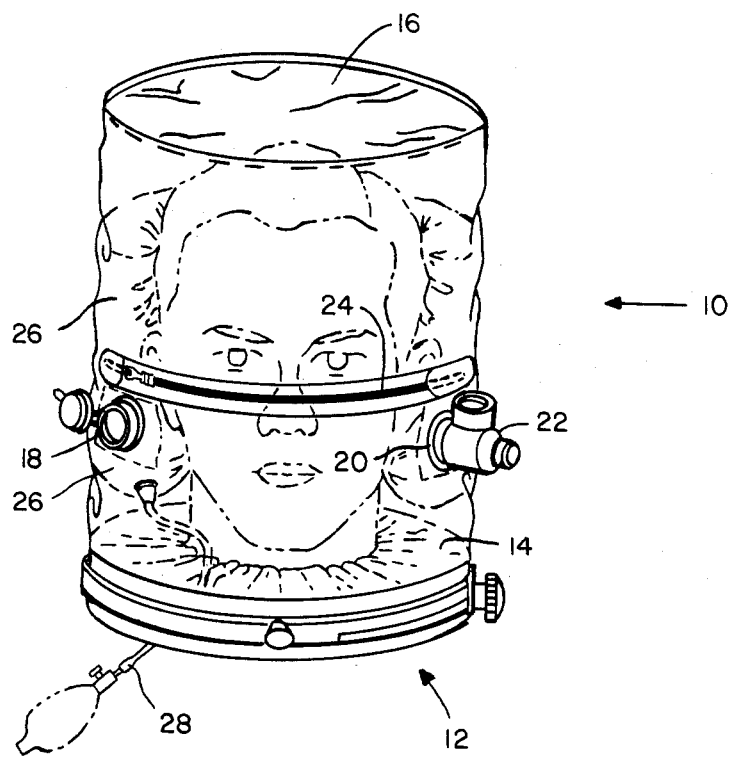
FIG. 1 is a front perspective view of the present invention.

Referring to the front perspective view of FIG. 1, there is shown a sealable hood assembly 10 for use in hyperbaric oxygen therapy, comprising a neckdam 12, having a diaphragm 14 coupled thereto. Also coupled to the neckdam is a hood 16 having oxgen inlet 18 and air exhaust 20. The hood 16 as shown in FIG. 1, comprises a clear, flexible, plastic cylinder having a closed top and an open base. Preferably a check valve 22 is mounted at exhaust 20 to guard against excessive air flow through the hood assembly. A zipper 24 provides access to the patient through the hood face. Also, an inflatable bladder 26 is preferably affixed to the rear of the hood and is provided with an inflation bulb 28 couplable thereto for manual inflation of the bladder.

The present invention can be used to comfortably treat litter-bound patients. Hence the bladder, acting as a pillow, comfortably maintains the prone patient's head in proper position within assembly 10.

Figure 2:
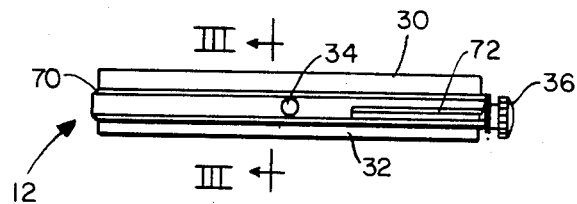
FIG. 2 is a front plan view of the neckdam of the invention.

Referring to FIG. 2, a front plan view of neckdam 12 is shown, comprising an upper ring 30 and a lower ring 32. These rings are disposed to rotate relative to each other by an amount of up to 180°, for purposes described in detail below. Also provided is a holding knob 34 affixed to upper ring 30 and a tightening knob 36 which is adjustedly mounted to lower ring 32 in a manner described below. A slot 72 is defined in upper ring 30 to facilitate assembly of rings 30, 32.

Figure 3:
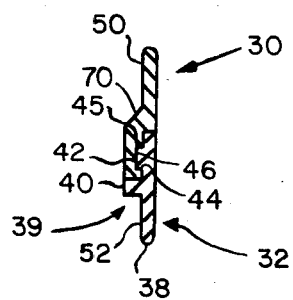
FIG. 3 is a left side cross-sectional view of the neckdam taken along line III—III of FIG. 2.

The neckdam rings 30, 32 are preferably fashioned out of light-weight PVC-type material and preferably mate, at least in part, in the manner indicated in the left-hand cross-sectional view of FIG. 3, taken along line III—III of FIG. 2. Hence, lower ring 32 will be seen to comprise a body 38 having an outer vertical surface 39 from which a horizontally projecting lip 40 is outwardly extended. Also, a second lip 42 is defined thereat above lip 40, wherein a channel 44 is created therebetween. Yet an additional channel 45 is defined at the top of lip 42.

Upper ring 30 comprises an inner vertical wall 46 which cooperates with wall 39 of ring 32 by means of complementary lips and channels defined therein. Upper ring 30 also defines a relatively broad flat outer vertical surface 50 and lower ring 32 defines a like surface 52, whose functions are described below. Hence, it will be appreciated that rings 30 and 32 matingly engage wherein each is rotatable relative to the other by means of respective cooperation of said lips and channels. This configuration is implemented in a 180° segment of each of the rings 30, 32, while a second 180° segment of each ring 30, 32 is differently configured, as described below.

Figure 4:
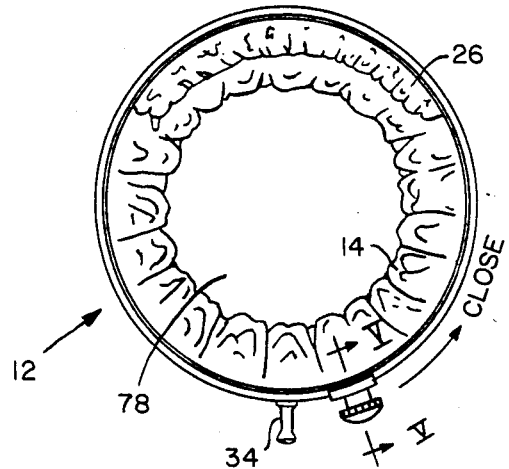
FIG. 4 is a top view of the neckdam with the diaphragm in an open condition and the bladder deflated.

Referring now to FIG. 4, there is shown a top view of neckdam 12 with the diaphragm in an open condition and the bladder deflated. In this figure, the rings are shown in the condition where the diaphragm is at its greatest aperture. In this position of the two rings 30, 32, the knob 34, 36 are circumferentially offset from each other. In this condition, the diaphragm will tend to blouse, as illustrated in this figure.

Figure 5:
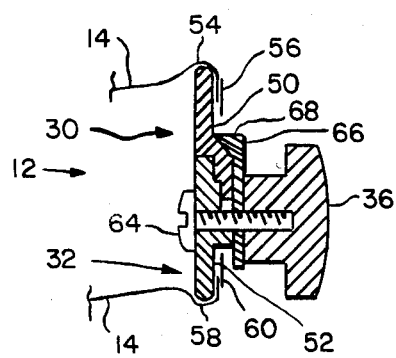
FIG. 5 is a right side cross-sectional view of the neckdam taken along line V—V of FIG. 4.

As seen in the right-hand cross-sectional view of FIG. 5, taken along the line V—V of FIG. 4, the two rings' second respective 180° segments are shown in cross-section, where the upper and lower borders of diaphragm 14 are affixed to neckdam 12 at ring faces 50 and 52, respectively. More particularly, diaphragm 14 may be understood to be a plastic cylinder, such as a plastic bag with the bottom removed. The diaphragm 14 is placed inside neckdam 12 and the upper border 54 of the diaphragm is folded over ring 30. Preferably a double sided tape has been applied to ring faces 50 and 52, respectively, and thence upper border 54 may be affixed to face 50 by pressing same together. A band of adhesive tape 56 may be applied thereat to the exposed diaphragm upper border to assure proper affixation thereof. In a like manner, the diaphragm lower border 58 is affixed to taped face 52 with tape 60 applied thereto.

Knob 36 is mounted to lower ring 32 by means of screw 64 threadedly engaging knob 36 through ring 32 and an intermediate washer 66. Assuming that knob 36 is not tightened down, rotation of one ring as to the other may be accomplished by grasping of knob 34, affixed to the upper ring 30, and rotating the lower ring 32 around the axis of the neck of the patient by pulling of knob 36 to the left or right.

It will now be understood that rings 30 and 32 are each comprised of two cooperating segments. Ring 30 is configured in a first 180° segment, starting from knob 36 and extending 90° left and right, according to as it is shown in FIG. 3. Configuration of the second 180° segment of ring 30 is as it is shown in the cross-section of FIG. 5. Likewise, ring 32 is configured in a first 180° segment, starting from knob 34 and extending 90° left and right, according to as it is shown in FIG. 3. Configuration of the second 180° segment of ring 32 is as it is shown in the cross-section of FIG. 5.

As a result of the cooperation of rings 30 and 32 and slot 72, the separate rings may be mated together to assemble a neckdam 12. When appropriate 180° sections of the upper and lower rings are properly oriented, at slot 72, then the rings seat easily together. Thereafter, as one ring is rotated, the cooperating lips and channels described earlier will interlock, thus interlocking rings 30 and 32. To provide greater interlock security, intermediate washer 66 defines a flange 68 at its upper border. This flange rides on inclined face 70 of ring 30 and serves to retain the rings together regardless of their rotational orientation by acting against the tendency of the rings to separate at slot 72.

Diaphragm 14 is affixed to neckdam 12 in a manner earlier described at a time when the rings 30 and 32 are oriented such that the lips and channels thereof are not interlocking. This defines the most open condition of diaphragm 14. As the rings are rotated relative to each other, the diaphragm (suspended as it is between rings 30 and 32) is twisted and becomes taught. This twisting occurs as tension increases in the fabric of diaphragm 14 between its upper and lower borders 56 and 58, respectively.

Figure 6:
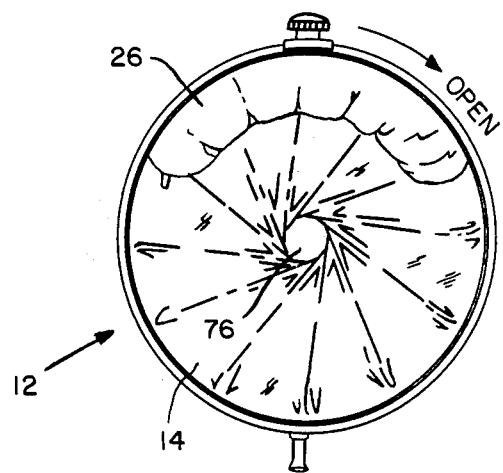
FIG. 6 is a top view of the neckdam with the diaphragm in a substantially closed condition and the bladder inflated.

FIG. 6 is a top view of neckdam 12 with diaphragm 14 in a twisted condition, thus rendering its open area 76 constricted compared to the unconstricted area 78 shown in FIG. 4. Also as seen in FIG. 6, the bladder 26 is inflated. It will be further understood that the diaphragm is generally sphincter-like in function, and it will be appreciated that its constricted condition is achieved when the rings are in an orientation removed from the assembly position of the rings described earlier. Furthermore, preferably a stop is provided to prevent further tightening of the diaphragm beyond a maximally constricted condition.

In operation, hood 16 is pulled over and taped to the upper ring 30 of an assembled neckdam 12 with the diaphragm 14 already affixed to the neckdam. The device is placed over the head of the patient, and then the holding knob 34 is grasped and held while the tightening knob 36 of the lower ring is grasped and pulled laterally. Hence, as the lower ring is rotated, the diaphragm closes snugly on the neck of the patient. Knob 36 is screwed tight thereafter which prevents further rotation of the rings. For an ambulatory patient, the neckdam also functions as a structural support, whereby the entire assembly may rest upon the patient's shoulder. For a litter patient, the bladder is pumped up like a pillow and locates the patient's head comfortably at the central axis of the hood. In either case, an oxygen hose is coupled to the assembly 10 at inlet 18 and an exhaust hose is coupled to valve 22. To remove hood assembly 10, the pillow is deflated, the tightening knob 36 is loosened, and the lower ring is rotated to achieve the open condition of the diaphragm. The hood assembly may then be removed either by the patient or by an assistant.

Furthermore, while the present invention has been described in connection with rather specific embodiments thereof, it will be understood that many modifications and variations will be readily apparent to those of ordinary skill in the art and that this application is intended to cover any adaptation or variation thereof. Therefore, it is manifestly intended that this invention be only limited by the claims and the equivalents thereof.

What is claimed is:

1. A lightweight therapeutic hood assembly comprising:
    (a) a lightweight ring mechanism comprising first and second mating rings rotatably secured to each other for encircling a patient's neck;
    (b) a flexible, transparent plastic hood portion attached to one of said rings for enveloping the patient's head;
    (c) plastic diaphragm means attached to the other of said rings which in conjunction with relative rotation of said first and second mating rings forms a substantially airtight seal around the patient's neck which, in conjunction with the hood portion, forms a sealed environment around the patient's head;
    (d) inflatable bladder means attached to the interior of said hood portion for positioning the patient's head within said hood portion with the diaphragm means secured around the patient's neck ;
    (e) a therapeutic gas inlet connected to said hood portion for introducing a pressurized therapeutic gas into said hood assembly containing the patient's head; and
    (f) a gas exit connected to said hood portion which promotes circulation of said therapeutic gas through said hood assembly.

2. The lightweight therapeutic hood assembly of claim 1 further comprising a check valve at said gas exit to promote unidirectional circulation of said therapeutic gas through said hood assembly.

3. The lightweight therapeutic hood assembly of claim 1 further comprising a resealable aperture in said hood portion for permitting immediate access to the patient.

4. The lightweight therapeutic hood assembly of claim 1 wherein said pressurized therapeutic gas comprises oxygen.

5. The lightweight therapeutic hood assembly of claim 1 wherein said device is used for hyperbaric oxygen therapy.

* * * * *